United States Patent
Hossainy

(10) Patent No.: US 6,896,965 B1
(45) Date of Patent: May 24, 2005

(54) RATE LIMITING BARRIERS FOR IMPLANTABLE DEVICES

(75) Inventor: Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 26 days.

(21) Appl. No.: 10/293,064

(22) Filed: Nov. 12, 2002

(51) Int. Cl.⁷ .......................... A61F 2/02; B32B 27/18; B32B 27/30; B32B 27/36
(52) U.S. Cl. .................... 428/411.1; 428/480; 428/500; 428/522; 623/1.15; 623/1.42; 623/1.44; 623/1.46
(58) Field of Search ............................. 623/1.15, 1.42, 623/1.44, 1.46; 428/36.91, 411.1, 480, 500, 522

(56) References Cited

U.S. PATENT DOCUMENTS

| | | | |
|---|---|---|---|
| 4,678,468 A | * 7/1987 | Hiroyoshi .................. | 623/1.49 |
| 4,816,339 A | * 3/1989 | Tu et al. ..................... | 428/421 |
| 4,931,287 A | 6/1990 | Bae et al. ................... | 424/484 |
| 4,977,901 A | 12/1990 | Ofstead ...................... | 128/772 |
| 5,112,457 A | 5/1992 | Marchant .................... | 204/165 |
| 5,328,471 A | 7/1994 | Slepian ....................... | 604/101 |
| 5,455,040 A | 10/1995 | Marchant .................... | 424/426 |
| 5,464,650 A | 11/1995 | Berg et al. .................. | 427/2.3 |
| 5,578,073 A | 11/1996 | Haimovich et al. ........... | 623/1 |
| 5,605,696 A | 2/1997 | Eury et al. .................. | 424/423 |
| 5,667,767 A | 9/1997 | Greff et al. ............... | 424/9.411 |
| 5,670,558 A | 9/1997 | Onishi et al. ............... | 523/112 |
| 5,700,286 A | 12/1997 | Tartaglia et al. ............. | 623/1 |
| 5,716,981 A | 2/1998 | Hunter et al. ............... | 514/449 |
| 5,824,049 A | 10/1998 | Ragheb et al. ................ | 623/1 |
| 5,830,178 A | 11/1998 | Jones et al. .................. | 604/49 |
| 5,837,313 A | 11/1998 | Ding et al. ................. | 427/2.21 |
| 5,851,508 A | 12/1998 | Greff et al. ............... | 424/9.411 |
| 5,858,746 A | 1/1999 | Hubbell et al. ............. | 435/177 |
| 5,865,814 A | 2/1999 | Tuch .......................... | 604/265 |
| 5,873,904 A | 2/1999 | Ragheb et al. ................ | 623/1 |
| 5,962,007 A | * 10/1999 | Cooper et al. .............. | 424/426 |
| 5,971,954 A | 10/1999 | Conway et al. ............... | 604/96 |
| 5,980,928 A | 11/1999 | Terry .......................... | 424/427 |
| 5,980,972 A | 11/1999 | Ding ......................... | 427/2.24 |
| 6,015,541 A | 1/2000 | Greff et al. ................. | 424/1.25 |
| 6,042,875 A | 3/2000 | Ding et al. ................. | 427/2.24 |
| 6,051,648 A | 4/2000 | Rhee et al. ................. | 525/54.1 |
| 6,056,993 A | 5/2000 | Leidner et al. ............. | 427/2.25 |
| 6,060,451 A | 5/2000 | DiMaio et al. ................ | 514/13 |
| 6,080,488 A | 6/2000 | Hostettler et al. ........ | 428/423.3 |
| 6,096,070 A | 8/2000 | Ragheb et al. .................. | 623/1 |
| 6,099,562 A | 8/2000 | Ding et al. ................. | 623/1.46 |
| 6,110,188 A | 8/2000 | Narciso, Jr. .................. | 606/153 |
| 6,113,629 A | 9/2000 | Ken .......................... | 623/1.1 |
| 6,120,536 A | 9/2000 | Ding et al. ................. | 623/1.43 |
| 6,120,904 A | 9/2000 | Hostettler et al. ........ | 428/423.3 |
| 6,121,027 A | 9/2000 | Clapper et al. ............. | 435/180 |
| 6,129,761 A | 10/2000 | Hubbell ....................... | 623/11 |
| 6,153,252 A | 11/2000 | Hossainy et al. ............ | 427/2.3 |
| 6,165,212 A | 12/2000 | Dereume et al. ........... | 623/1.13 |

FOREIGN PATENT DOCUMENTS

| | | |
|---|---|---|
| EP | 0 665 023 | 8/1995 |
| EP | 0 970 711 | 1/2000 |
| WO | WO 00/12147 | 3/2000 |
| WO | WO 00/64506 | 11/2000 |
| WO | WO 01/01890 | 1/2001 |

* cited by examiner

*Primary Examiner*—Ramsey Zacharia
(74) *Attorney, Agent, or Firm*—Squire, Sanders & Dempsey L.L.P.

(57) ABSTRACT

A coating for implantable medical devices including an interpenetrating polymer network serving as a rate limiting barrier.

9 Claims, No Drawings

RATE LIMITING BARRIERS FOR IMPLANTABLE DEVICES

BACKGROUND OF THE INVENTION

1. Field of the Invention

This invention relates to coatings for controlling the rate of release of drugs from implantable medical devices such as stents.

2. Description of Related Art

In the field of medical-technology, there is frequently a necessity to administer drugs locally. To provide an efficacious concentration to the treatment site, systemic administration of medication can produce adverse or toxic side effect for the patient. Local delivery is a preferred method of treatment in that smaller total levels of medication are administered in comparison to systemic dosages, but are concentrated at a specific site.

In the treatment of vascular disorders, such as arteriosclerosis, intracoronary stents are now a standard adjunct to balloon angioplasty. Stenting eliminates vasospasm, tacks dissections to the vessel wall, and reduces negative remodeling. Stents can be made from interconnected struts that are usually between 50 and 150 microns wide. Being made of a metal (for instance, stainless steel), bare stents have to be modified so as to provide a means for local drug delivery. Accordingly, stents are being modified by forming a polymer coating, containing a drug, on the surface of the stent.

A coating used to achieve local drug delivery via stent can include a three-layer structure. The three layer structure includes a drug-polymer layer serving as a reservoir for the drug, an optional primer polymer layer for improving adhesion of the drug-polymer layer to the surface of the stent, and an optional topcoat polymer layer for reducing the rate of release of the drug. The medicine to be administered will have a sustained release profile from drug-polymer layer through the topcoat polymer layer.

To the extent that the mechanical functionality of stents has been optimized in recent years, it has been determined that continued improvements could be done by means of pharmacological therapies. For the purposes of pharmacological therapy, it is important to maintain the concentration of the drug at a therapeutically effective level for an acceptable period of time. Hence, controlling a rate of release of the drug from the stent is important, especially in such a way so as to decrease the release rate of the drug from the matrix. In view of the foregoing, coatings for reducing the rate of release a therapeutic substance from implantable devices, such as stents, are desired. The coatings should prolong the residence time of the drug in the patient, among other useful functions.

SUMMARY

According to one embodiment of the present invention, a multi-layer coating for an implantable medical device is provided, wherein the outermost layer of the coating includes an interpenetrating polymer network. The interpenetrating polymer network can be formed from a product selected from a group consisting of poly(ethylene glycol)-acrylate, poly(ethylene glycol)-methacrylate, poly(ethylene glycol)-diacrylate, poly(ethylene glycol)-dimethacrylate, N-vinylpyrrolidone, heparin, and heparin derivatives, hyaluronic acid, derivatives of hyaluronic acid, poly (butyleneterephthalate-co ethylene glycol) (PBT-PEG), and mixtures thereof.

According to another embodiment of the present invention, a method for fabricating a coating on an implantable medical device is provided, the method comprises forming a first polymer layer on the device, applying on the first polymer layer a precursor of an interpenetrating polymer network, subjecting the device to a treatment to cause the precursor to form the interpenetrating polymer network on the device.

DETAILED DESCRIPTION

A coating for an implantable medical device, such as a stent, can include an optional primer layer, a drug-polymer layer, a topcoat layer, and an optional finishing coat layer. The drug-polymer layer can be applied directly onto the stent to serve as a reservoir for the sustained release of a therapeutic agent. The topcoat layer can serve as a rate limiting membrane which controls the rate of release of the drug. The optional primer layer can be applied between the stent and the drug-polymer layer to improve the adhesion of the coating to the stent. The finishing coat layer can be applied over the topcoat layer and can be used for improving the biocompatibility of the underlying layer.

The process of the release of the drug from a coating having both topcoat and finishing coat layers includes at least three distinctive steps. First, the drug is absorbed by the polymer of the topcoat layer on the drug-polymer layer/topcoat layer interface. Next, the drug diffuses through the topcoat layer using empty spaces between the macromolecules of the topcoat layer polymer as pathways for migration. Next, the drug arrives to the topcoat layer/finishing layer interface. Finally, the drug diffuses through the finishing coat layer in a similar fashion, arrives to the outer surface of the finishing coat layer, and desorbs from the outer surface. At this point, the drug is released into the blood stream. Consequently, a combination of the topcoat and finishing coat layers, if used, can serve as a rate limiting barrier.

The total amount of the drug in the coating can be between about 0.02 and 2.0% by mass, for example, between 0.7 and 1.2%. The drug can include any substance capable of exerting a therapeutic or prophylactic effect for a patient. The drug may include small molecule drugs, peptides, proteins, oligonucleotides, and the like. The drug could be designed, for example, to inhibit the activity of vascular smooth muscle cells. It can be directed at inhibiting abnormal or inappropriate migration and/or proliferation of smooth muscle cells to inhibit restenosis.

Examples of drugs include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S. A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Corn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O-[2-(2-hydroxy)ethoxy] ethyl-rapamycin, and 40-O-tetrazole-rapamycin.

Poly(ethylene-co-vinyl alcohol) (EVAL) is one example of a polymer that can be included in the drug-polymer layer, the optional primer layer, the topcoat layer and the finishing coat layer. EVAL has the general formula $-[CH_2-CH_2]_m-[CH_2-CH(OH)]_n-$. EVAL is a product of hydrolysis of ethylene-vinyl acetate copolymers and may also be a terpolymer including up to 5 molar % of units derived from styrene, propylene and other suitable unsaturated monomers. A brand of copolymer of ethylene and vinyl alcohol distributed commercially under the trade name EVAL by Aldrich Chemical Co. of Milwaukee, Wis., and manufactured by EVAL Company of America of Lisle, Ill., can be used.

Other suitable polymers can also be used for making a drug-polymer layer, the optional primer layer, the topcoat layer and the finishing coat layer. Representative examples include poly(hydroxyvalerate), poly(L-lactic acid), polycaprolactone, poly(lactide-co-glycolide), poly (hydroxybutyrate), poly(hydroxybutyrate-co-valerate), polydioxanone, polyorthoesters, polyanhydride, poly (glycolic acid), poly(D,L-lactic acid), poly(glycolic acid-co-trimethylene carbonate), polyphosphoesters, polyphosphoester urethanes, poly(amino acids), cyanoacrylates, poly (trimethylene carbonate), poly(iminocarbonate), co-poly (ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinylidene halides (such as polyvinylidene fluoride and polyvinylidene chloride), polyvinyl ethers (such as polyvinyl methyl-ether), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as NYLON 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellulose nitrate, cellulose propionate, cellulose ethers, carboxymethyl cellulose, CELLOPHANE and mixtures thereof.

Poly(ethylene glycol) (PEG) is one example of a polymer that can be included in the topcoat layer and/or the finishing coat layer. PEG is a biologically compatible product having the formula $H-[O-CH_2-CH_2-O-CH_2-CH_2]_n-OH$, and can have a molecular weight within a range of between about 1,000 and about 100,000 Daltons, for example, between 2,000 and 10,000 Daltons, such as 5,000 Daltons. The value of the integer "n" in the formula of PEG is about 56 for PEG having molecular weight of about 5,000.

Other suitable polymers can also be used to form in the topcoat layer and/or the finishing coat layer. Representative examples include heparin, hyaluronic acid, and silk-elastin protein block-copolymer. Heparin comprises a mixture of sulfated polysaccharide chains based on D-glucosamine and D-glucuronic or L-iduronic acid. A brand of heparin known under the trade name DURAFLO can be used. DURAFLO can be obtained from Baxter Healthcare Corporation of Deerfield, Ill. Hyaluronic acid is a linear polysaccharide composed of disaccharide units of N-acetylglucosamine and D-glucuronic acid. In hyaluronic acid, uronic acid and the aminosugar are linked by alternating $\beta$-1,4 and $\beta$-1,3 glucosidic bonds. Silk-elastin protein block-copolymers combine the repeating blocks of amino acids thus providing the copolymer with the, mechanical strength characterizing silk and the flexibility characterizing elastin. Silk-elastin block-copolymer can be obtained from Protein Polymer Technologies, Inc. of San Diego, Calif.

According to an embodiment of the present invention, the stent coating can comprise interpenetrating polymer networks (IPN). For the purposes of the present invention, a definition of the IPN used by the International Union of Pure and Applied Chemistry (IUPAC) is adopted. The IUPAC describes the IPN as a polymer comprising two or more networks which are at least partially interlaced on a molecular scale, but not covalently bonded to each other and cannot be separated unless chemical bonds are broken. In other words, an IPN structure represents two or more polymer networks that are physically entangled. One example of an IPN that can be used is a surface hydrogel.

One example of a product that can be used for forming the IPN is a PEG-based unsaturated product, for example, pre-polymer of PEG-acrylate or methacrylate having a general formula $CH_2=CX-COO-[CH_2-CH_2-O]_n-H$, where X is hydrogen (acrylates) or methyl (methacrylates). Weight average molecular weight of PEG-acrylate or methacrylate can be within a range of about 10,000 to 100,00 Daltons. PEG-acrylate prepolymer can be applied on the surface of the drug-polymer or topcoat layer and cured, for example, using a radical initiator which is activated by UV radiation (UV initiators), light (light initiators), or heat (thermal initiators). Examples of appropriate initiators include acetophenone, 2,2-dimethoxy-2-phenol-acetophenone (UV initiators), camproquinone, ethyl-4-N, N,-dimethyl aminobenzoate (light initiators), and benzoyl peroxide (thermal initiator). As a result of the curing process, PEG-acrylate will partially cross-link and partially physically entangle with the polymer of the underlying layer thus forming the outermost coat layer which includes an IPN. PEG-acrylate or methacrylate is intended to broadly include poly(ethylene glycol)-diacrylate (PEG-diacrylate) and poly(ethylene glycol)-dimethacrylate (PEG-dimethacrylate). PEG-acrylate or methacrylate and PEG-diacrylate or dimethacrylate can be optionally terminated, for example, with stearic acid, to form PEG-acrylate-stearate PEG-methacrylate-stearate, respectively.

Examples of other products that can be used for forming the IPN include such unsaturated reactive products as N-vinylpyrrolidone, heparin and its derivatives, hyaluronic acid and its derivatives, some hydrogel-forming products such as poly(butyleneterephthalate-co ethylene glycol) (PBT-PEG), and mixtures of any of these products with each other or with PEG-acrylate or methacrylate.

Suitable derivatives of heparin include sodium heparin (Na—Hep), heparin benzalkonium chloride (HBAC), and heparin tridodecyl methyl ammonium chloride (HTDMAC). Derivatives of heparin can also include heparin modified by introduction of photoactivatable groups in the heparin molecule (the groups that are inactive under ambient conditions but become reactive when irradiated by UV-light, for example, at the frequency of about 360 nm). Examples of photoactivatable groups include groups derived from benzophenone or dithiocarbonate. Methods of introducing the photoactivatable groups into the molecules of heparin are known to those having ordinary skill in the art. Other derivatives of heparin can include heparin containing a moiety that tends to bind to albumin, for example a the —$(CH_2)_{18}$—moiety.

The coatings of all the embodiments of the present invention have been described in conjunction with a stent. However, the coatings can also be used with a variety of other medical devices. Examples of the implantable medical device, that can be used in conjunction with the embodiments of this invention include stent-grafts, grafts (e.g., aortic grafts), artificial heart valves, cerebrospinal fluid shunts, pacemaker electrodes, coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35 N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

EXAMPLES

Embodiments of the present invention can be further illustrated by the following Examples.

Example 1

A first composition can be prepared by mixing the following components:

(a) between about 0.1 mass % and about 15 mass %, for example, about 2.0 mass % of EVAL;

(b) between about 0.05 mass % and about 1.0 mass %, for example, about 1.0 mass % of EVEROLIMUS; and (c) the balance, dimethylacetamide (DMAC) solvent.

The first composition can be applied onto the surface of a stent (with or without the primer layer) and dried, to form a drug-polymer layer, for example, by spraying. An EFD spray head can be used, having a 0.014 inch fan nozzle with a feed pressure of about 0.2 atm (3 psi) and an atomization pressure of between-about 1 atm and 1.3 atm (15 to 20 psi). The total amount of solids of the drug-polymer layer can be about 300 micrograms ($\mu$g). "Solids" is defined as the amount of the dry residue deposited on the stent after all volatile organic compounds (e.g., the solvent) have been removed.

A second composition can be prepared by mixing the following components:

(d) between about 0.1 mass % and about 15 mass %, for example, about 2.0 mass % of EVAL; and (e) the balance of DMAC solvent.

The second composition can be applied onto the dried drug-polymer layer, for example, by spraying or dipping, to form the topcoat layer. The topcoat layer can have, for example, a total solids weight of about 250 $\mu$g.

A third composition can be prepared by mixing the following components:

(g) between about 0.1 mass % and about 15 mass %, for example, about 2.0 mass % of EVAL;

(h) between about 0.1 mass % and about 5 mass %, for example, about 1.0 mass % of DURAFLO;

(i) between about 25 mass % and about 30 mass %, for example, 27.85 mass % of dimethylsulfoxide (DMSO) solvent;

(j) between about 5 mass % and about 6 mass %, for example, 5.65 mass % of tethrahydrofurane (THF) solvent; and (k) the balance, DMAC solvent.

The third composition can be applied onto the dried topcoat layer, for example, by spraying or dipping, to form the finishing coat layer having a total solids weight of about 200 $\mu$g.

Example 2

A first composition can be prepared by mixing the following components:

(a) between about 0.1 mass % and about 15 mass %, for example, about 2.0 mass % of EVAL;

(b) between about 0.05 mass % and about 1.0 mass %, for example, about 0.7 mass % of EVEROLIMUS; and (c) the balance, DMAC solvent.

The first composition can be applied onto a stent as described in Example 1, for example, by spraying, to form a drug-polymer layer with about 100 fig of total solids.

A second composition can be prepared by mixing the following components:

(d) between about 0.1 mass % and about 15 mass %, for example, about 2 mass % of EVAL; and (e) the balance, DMAC solvent.

The second composition can be applied onto the dried drug-polymer layer, for example, by spraying, to form the topcoat layer having a total solids weight of about 300 $\mu$g.

A third composition can be prepared by mixing the following components:

(f) between about 0.1 mass % and about 15 mass %, for example, about 2.0 mass % of EVAL;

(g) between about 0.1 mass % and about 5 mass %, for example, about 1.0 mass % of poly(ethylene glycol) having molecular weight of about 5,000 Daltons (PEG5000); and (h) the balance, DMAC solvent.

The third composition can be applied onto the dried topcoat layer, for example, by spraying or dipping, to form the finishing coat layer having a total solids weight of about 200 µg.

Example 3

A first composition can be prepared by mixing the following components:

(a) between about 0.1 mass % and about 15 mass %, for example, about 2.0 mass % of EVAL;

(b) between about 0.05 mass % and about 1.0 mass %, for example, about 0.7 mass % of EVEROLIMUS; and (c) the balance, DMAC solvent.

The first composition can be applied onto a stent as described in Example 1, for example, by spraying, to form a drug-polymer layer with about 200 µg of total solids.

A second composition can be prepared by mixing the following components:

(d) between about 0.1 mass % and about 15 mass %, for example, about 2 mass % of EVAL; and (e) the balance, DMAC solvent.

The second composition can be applied onto the dried drug-polymer layer, for example, by spraying, to form the topcoat layer having a total solids weight of about 300 µg.

A third composition can be prepared by mixing the following components:

(f) between about 0.1 mass % and about 15 mass %, for example, about 1.3 mass % of EVAL;

(g) between about 0.1 mass % and about 5 mass %, for example, about 0.7 mass % of PEG5000; and (h) the balance, DMAC solvent.

The third composition can be applied onto the dried topcoat layer, for example, by spraying or dipping, to form the finishing coat layer having a total solids weight of about 200 µg.

Example 4

A stent can be coated as described in Example 3, except the drug-polymer layer can have a total solids weight of about 400 pug, and the finishing coat layer can have a total solids weight of about 150 µg.

Example 5

A first composition can be prepared by mixing the following components:

(a) between about 0.1 mass % and about 15 mass %, for example, about 2.0 mass % of EVAL;

(b) between about 0.05 mass % and about 1.5 mass %, for example, about 1.2 mass % of EVEROLIMUS; and (c) the balance, DMAC solvent.

The first composition is applied onto a stent as described in Example 1, for example, by spraying, to form a drug-polymer layer with about 420 µg of total solids.

A second composition can be prepared by mixing the following components:

(d) between about 0.1 mass % and about 15 mass %, for example, about 2 mass % of EVAL; and (e) the balance, DMAC solvent.

The second composition can be applied onto the dried drug-polymer layer, for example, by spraying, to form the topcoat layer having a total solids weight of about 300 µg.

A third composition can be prepared by mixing the following components:

(f) between about 0.1 mass % and about 15 mass %, for example, about 1.3 mass % of EVAL;

(g) between about 0.1 mass % and about 5 mass %, for example, about 0.7 mass % of PEG5000; and (h) the balance, DMAC solvent.

The third composition can be applied onto the dried topcoat layer, for example, by spraying or dipping, to form the finishing coat layer having a total solids weight of about 150 µg.

Example 6

A first composition can be prepared by mixing the following components:

(a) between about 0.1 mass % and about 15 mass %, for example, about 1.4 mass % of EVAL;

(b) between about 0.05 mass % and about 1.5 mass %, for example, about 0.7 mass % of the drug β-estradiol; and (c) the balance, DMAC solvent.

The first composition can be applied onto a stent as described in Example 1, for example, by spraying, to form a drug-polymer layer with about 450 µg of total solids.

A second composition can be prepared by mixing the following components:

(d) between about 0.1 mass % and about 15 mass %, for example, about 2 mass % of EVAL; and (e) the balance, DMAC solvent.

The second composition can be applied onto the dried drug-polymer layer, for example, by spraying, to form the topcoat layer having a total solids weight of about 250 µg.

A third composition can be prepared by mixing the following components:

(f) between about 0.1 mass % and about 15 mass %, for example, about 1.3 mass % of EVAL;

(g) between about 0.1 mass % and about 5 mass %, for example, about 0.7 mass % of PEG5000; and (h) the balance, DMAC solvent.

The third composition can be applied onto the dried topcoat layer, for example, by spraying or dipping, to form the finishing coat layer having a total solids weight of about 150 µg.

Example 7

A first composition can be prepared by mixing the following components:

(a) between about 0.1 mass % and about 15 mass %, for example, about 1.0 mass % of EVAL;

(b) between about 0.05 mass % and about 1.5 mass %, for example, about 1.0 mass % of O-estradiol; and (c) the balance, DMAC solvent.

The first composition can be applied onto a stent as described in Example 1, for example, by spraying, to form a drug-polymer layer with about 320 µg of total solids.

A second composition can be prepared by mixing the following components:

(d) between about 0.1 mass % and about 15 mass %, for example, about 2 mass % of EVAL; and (e) the balance, DMAC solvent.

The second composition can be applied onto the dried drug-polymer layer, for example, by spraying, to form the topcoat layer having a total solids weight of about 250 µg.

A third composition can be prepared by mixing the following components:

(f) between about 0.1 mass % and about 15 mass %, for example, about 1.3 mass % of EVAL;

(g) between about 0.1 mass % and about 5 mass %, for example, about 0.7 mass % of PEG5000; and (h) the balance, DMAC solvent.

The third composition can be applied onto the dried topcoat layer, for example, by spraying or dipping, to form the finishing coat layer having a total solids weight of about 150 µg.

Example 8

A first composition can be prepared by mixing the following components:

(a) between about 0.1 mass % and about 15 mass %, for example, about 1.0 mass % of EVAL;

(b) between about 0.05 mass % and about 1.5 mass %, for example, about 1.0 mass % of β-estradiol; and (c) the balance, DMAC solvent.

The first composition can be applied onto a stent as described in Example 1, for example, by spraying, to form a drug-polymer layer with about 200 µg of total solids.

A second composition can be prepared by mixing the following components:

(d) between about 0.1 mass % and about 15 mass %, for example, about 2 mass % of EVAL; and (e) the balance, DMAC solvent.

The second composition can be applied onto the dried drug-polymer layer, for example, by spraying, to form the topcoat layer having a total solids weight of about 200 µg.

A third composition can be prepared by mixing the following components:

(f) between about 0.1 mass % and about 15 mass %, for example, about 0.5 mass % of EVAL;

(g) between about 0.1 mass % and about 5 mass %, for example, about 0.25 mass % of hyaluronic acid; and (h) the balance, DMSO solvent.

The third composition can be applied onto the dried topcoat layer, for example, by centrifugation, to form the finishing coat layer having a total solids weight of about 150 µg. The method of coating by centrifugation is known to those having ordinary skill in the art.

Example 9

A stent can be coated as described in Example 8, except the drug-polymer and the topcoat layer each can have a total solids weight of about 100 µg.

Example 10

A first composition can be prepared by mixing the following components:

(a) between about 0.1 mass % and about 15 mass %, for example, about 1.3 mass % of EVAL;

(b) between about 0.05 mass % and about 1.5 mass %, for example, about 0.7 mass % of β-estradiol; and (c) the balance, DMAC solvent.

The first composition can be applied onto a stent as described in Example 1, for example, by spraying, to form a drug-polymer layer with about 200 µg of total solids.

A second composition can be prepared by mixing the following components:

(d) between about 0.1 mass % and about 15 mass %, for example, about 2 mass % of EVAL; and (e) the balance, DMAC solvent.

The second composition can be applied onto the dried drug-polymer layer, for example, by spraying, to form the topcoat layer having a total solids weight of about 200 µg.

A third composition can be prepared by mixing the following components:

(f) between about 0.1 mass % and about 15 mass %, for example, about 0.5 mass % of EVAL;

(g) between about 0.1 mass % and about 5 mass %, for example, about 0.25 mass % of hyaluronic acid; and (h) the balance, DMSO solvent.

The third composition can be applied onto the dried topcoat layer, for example, by centrifugation, to form the finishing coat layer having a total solids weight of about 150 µg.

Example 11

A first composition can be prepared by mixing the following components:

(a) between about 0.1 mass % and about 15 mass %, for example, about 1.0 mass % of EVAL;

(b) between about 0.05 mass % and about 1.5 mass %, for example, about 1.0 mass % of estradiol; and (c) the balance, DMAC solvent.

The first composition can be applied onto a stent as described in Example 1, for example, by spraying, to form a drug-polymer layer with about 200 µg of total solids.

A second composition can be prepared by mixing the following components:

(d) between about 0.1 mass % and about 15 mass %, for example, about 2 mass % of EVAL; and (e) the balance, DMAC solvent.

The second composition can be applied onto the dried drug-polymer layer, for example, by spraying, to form the topcoat layer having a total solids weight of about 200 µg.

A third composition can be prepared by mixing the following components:

(f) between about 0.1 mass % and about 15 mass %, for example, about 0.5 mass % of silk elastin product;

(g) between about 0.1 mass % and about 5 mass %, for example, about 0.5 mass % of hyaluronic acid; and (h) the balance, distilled water.

The third composition can be applied onto the dried topcoat layer, for example, by centrifugation, to form the finishing coat layer having a total solids weight of about 150 µg.

Example 12

A stent can be coated as described in Example 11, except the drug-polymer and the topcoat layer each can have a total solids weight of about 100 fig.

Example 13

A first composition can be prepared by mixing the following components:

(a) between about 0.1 mass % and about 15 mass %, for example, about 1.3 mass % of EVAL;

(b) between about 0.05 mass % and about 1.5 mass %, for example, about 0.7 mass % of β-estradiol; and (c) the balance, DMAC solvent.

The first composition can be applied onto a stent as described in Example 1, for example, by spraying, to form a drug-polymer layer with about 200 µg of total solids.

A second composition can be prepared by mixing the following components:

(d) between about 0.1 mass % and about 15 mass %, for example, about 2 mass % of EVAL; and (e) the balance, DMAC solvent.

The second composition can be applied onto the dried drug-polymer layer, for example, by spraying, to form the topcoat layer having a total solids weight of about 200 µg.

A third composition can be prepared by mixing the following components:

(f) between about 0.1 mass % and about 15 mass %, for example, about 0.5 mass % of silk elastin product (g) between about 0.1 mass % and about 5 mass %, for example, about 0.5 mass % of hyaluronic acid; and (h) the balance, distilled water.

The third composition can be applied onto the dried topcoat layer, for example, by centrifugation, to form the finishing coat layer having a total solids weight of about 150 µg.

Examples 1–13 are summarized in Table 1.

(c) the balance a solvent mixture, the mixture containing de-ionized water and ethanol in a mass ratio of about 4:1.

The composition can be applied on the dried drug-polymer layer and irradiated with UV-light at a wavelength of 360 nm for about 10 seconds, followed by drying, to form a topcoat layer comprising an IPN based on poly(PEG-acrylate).

Example 15

The stent can be coated as described in Example 14, except that the same amount of benzoyl peroxide can be used the instead of acetophenone. The topcoat layer-forming IPN can be formed by subjecting the stent to a temperature of about 80° C. for about 5 minutes.

Example 16

A drug-polymer layer can be formed on a stent as described in Example 1. A composition can be prepared, the composition including:

TABLE 1

A Summary of the Formulations of Examples 1–13

| Example | Drug-Polymer Layer | | | Topcoat Layer | | Finishing Coat Layer | |
|---|---|---|---|---|---|---|---|
| | Polymer, % | Drug, % | Weight of the layer, µg | Polymer, % | Weight of the layer, µg | Polymer, % | Weight of the layer, µg |
| 1 | EVAL, 2 | EVEROLIMUS, 1 | 300 | EVAL, 2 | 250 | EVAL, 2 DFLO, 1 | 200 |
| 2 | EVAL, 2 | EVEROLIMUS, 0.7 | 100 | EVAL, 2 | 300 | EVAL, 2 PEG500, 1 | 200 |
| 3 | EVAL, 2 | EVEROLIMUS, 0.7 | 20 | EVAL, 2 | 300 | EVAL, 1.3 PEG5000, 0.7 | 200 |
| 4 | EVAL, 2 | EVEROLIMUS, 0.7 | 400 | EVAL, 2 | 300 | EVAL, 1.3 PEG5000, 0.7 | 150 |
| 5 | EVAL, 2 | EVEROLIMUS, 1.2 | 420 | EVAL, 2 | 300 | EVAL, 1.3 PEG5000, 0.7 | 150 |
| 6 | EVAL, 1.4 | Estradiol, 0.7 | 450 | EVAL, 2 | 250 | EVAL, 1.3 PEG5000, 0.7 | 150 |
| 7 | EVAL, 1 | Estradiol, 1 | 320 | EVAL, 2 | 250 | EVAL, 1.3 PEG5000, 0.7 | 150 |
| 8 | EVAL, 1 | Estradiol, 1 | 200 | EVAL, 2 | 200 | EVAL, 0.5 Hyaluronic acid, 0.25 | 150 |
| 9 | EVAL, 1 | Estradiol, 1 | 100 | EVAL, 2 | 100 | EVAL, 0.5 Hyaluronic acid, 0.25 | 150 |
| 10 | EVAL, 1.3 | Estradiol, 0.7 | 150 | EVAL, 2 | 150 | EVAL, 0.5 Hyaluronic acid, 0.25 | 150 |
| 11 | EVAL, 1 | Estradiol, 1 | 200 | EVAL, 2 | 200 | Silk Elastin, 0.5 Hyaluronic acid, 0.5 | 150 |
| 12 | EVAL, 1 | Estradiol, 1 | 100 | EVAL, 2 | 100 | Silk Elastin, 0.5 Hyaluronic acid, 0.5 | 150 |
| 13 | EVAL, 1.3 | Estradiol, 0.7 | 200 | EVAL, 0.5 | 200 | Silk Elastin, 0.5 Hyaluronic acid, 0.5 | 150 |

Example 14

A drug-polymer layer can be formed on a stent as described in Example 1. A composition can be prepared, the composition including:

(a) about 3 mass % of PEG-acrylate having M, within a range of about 10,000 and 100,000;

(b) about 1 mass % of 2,2-dimethoxy-2-phenol-acetophenone; and (a) about 20 mass % of N-vinylpyrrolidone;

(b) about 3 mass % of PEG-acrylate having $M_w$ within a range of about 10,000 and 100,000;

(c) about 1 mass % of 2,2-dimethoxy-2-phenol-acetophenone; and (d) the balance of a solvent mixture, the mixture containing de-ionized water and ethanol in a mass ratio of about 4:1.

The composition can be applied on a stent and a topcoat layer comprising an IPN can be formed as described in Example 14.

Example 17

A drug-polymer layer can be formed on a stent as described in Example 1. A composition can be prepared, the composition including:

(a) about 3 mass % of PEG-acrylate having M, within a range of about 10,000 and 100,000;
(b) about 3 mass % of heparin benzalkonium chloride (HBAC);
(c) about 1 mass % of acetophenone; and
(d) the balance a solvent mixture, the mixture containing iso-propanol and dimethylacetamide in a mass ratio of about 14:1.

The composition can be applied on a stent and a topcoat layer comprising an IPN can be formed as described in Example 14.

Example 18

A drug-polymer layer can be formed on a stent as described in Example 1. A composition can be prepared, the composition including:

(a) about 2 mass % of EVAL;
(b) about 0.7 mass % of PEG having $M_t$ of about 17,500 Daltons;
(c) about 0.7 mass % of PEG-diacrylate having M, of about 10,000 Daltons;
(d) about 0.7 mass % of HBAC;
(e) about 0.1 mass % of 2,2-dimethoxy-2-phenol-acetophenone; and
(f) the balance dimethylacetamide solvent.

The composition can be applied on a stent and a topcoat layer comprising an IPN can be formed as described in Example 14.

Example 19

A drug-polymer layer can be formed on a stent as described in Example 1. A composition can be prepared, the composition including:

(a) about 7 mass % of EVAL;
(b) about 2 mass % of PEG having M, of about 17,500 Daltons;
(c) about 2 mass % of PEG-diacrylate having M, of about 10,000 Daltons;
(d) about 2 mass % of HBAC;
(e) about 0.5 mass % of 2,2-dimethoxy-2-phenol-acetophenone; and
(f) the balance dimethylacetamide solvent.

The composition can be applied on a stent by spin coating and a topcoat layer comprising an IPN can be formed.

Example 20

A drug-polymer layer can be formed on a stent as described in Example 1. A composition can be prepared, the composition including:

(a) about 2 mass % of EVAL;
(b) about 0.4 mass % of PEG having $M_w$ of about 17,500 Daltons;
(c) about 0.2 mass % of HBAC; and
(d) the balance of dimethylacetamide solvent.

The composition can be applied on a stent, for example, by spraying, to form a topcoat layer.

Example 21

A drug-polymer layer can be formed on a stent as described in Example 1. A composition can be prepared, the composition including:

(a) about 3 mass % of EVAL;
(b) about 2 mass % of PEG having $M_w$ of about 17,500 Daltons;
(c) about 2 mass % of sodium heparin (Na—Hep); and
(d) the balance, a solvent blend, the blend comprising formamide (FA), methanol (MeOH) and dimethylacetamide (DMAC) in a mass ratio FA:MeOH:DMAC of about 1:1.05:3.

To prepare the composition, Na—Hep can be dissolved in FA first at a temperature between about 60° C. and 100° C., to form about 10% Na—Hep/FA solution, followed by adding EVAL, PEG, MeOH and DMAC to the Na—Hep/FA solution.

The composition can be applied on a stent, for example, by spraying while the temperature of the composition is maintained between about 55° C. and 70° C., to form a topcoat layer.

Example 22

A first composition can be prepared, the composition including:

(a) about 2 mass % of PBT-PEG having the formula (1):

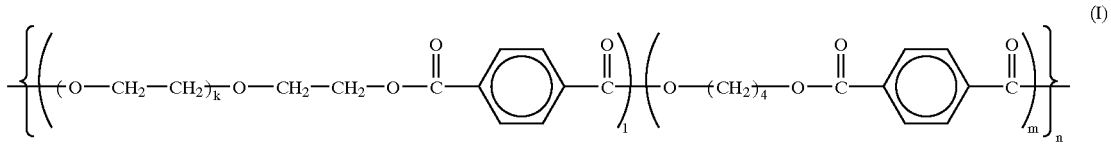

wherein k is about 90 (corresponding to number averaged molecular weight of the PEG fragment of about 4,000), the PBT-PEG polymer comprises about 80% units derived from PEG and about 20% units derived from butylene terephthalate;

(b) the balance, a solvent blend, the blend comprising trichloroethane and chloroform in a mass ratio between trichloroethane and chloroform of about 4:1.

The first composition can be applied onto the surface of a stent, for example, by spraying, and dried at about 140° C. for about 1 hour, to form a primer layer. An EFD spray head can be used, having a 0.014 fan nozzle with a feed pressure of about 0.2 atm (3 psi) and an atomization pressure of between about 1 atm and 1.3 atm (15 to 20 psi). The total amount of solids of the primer layer can be about 100 μg.

A second composition can be prepared, the composition including:

(a) about 2 mass % of PBT-PEG described above;
(b) about 1 mass % of EVEROLIMUS; and
(c) the balance, a solvent blend, the blend comprising trichloroethane and chloroform in a mass ratio between trichloroethane and chloroform of about 4:1.

The second composition can be applied onto the dried primer layer, for example, by spraying, and dried at about 50° C. for about 2 hours, to form a drug-polymer layer. The total amount of solids of the drug-polymer layer can be about 300 µg.

A third composition can be prepared, the composition including:
  (a) about 2 mass % of PBT-PEG described by the formula (1), wherein K is about 90, the PBT-PEG polymer comprises about 80% of units derived from PEG and about 20% of units derived from butylene terephthalate, and wherein $T_m$ of the PEG fragment is about 47° C., and $T_m$ of the butylene terephthalate fragment is about 173° C.
  (b) the balance, a 1,4-dioxane solvent blend.

The third composition can be applied onto the dry drug-polymer layer, for example, by spraying, and dried at about 50° C. for about 1 hour, to form a topcoat layer. The total amount of solids of the topcoat layer can be about 100 µg.

Examples 14–22 are summarized in Table 2.

TABLE 2

A Summary of the Formulations of Examples 14–22

| | Drug-Polymer Layer | | | Topcoat Layer | |
|---|---|---|---|---|---|
| Example | Polymer, % | Drug, % | Weight of the layer, µg | Products-Precursors for IPN | Amount, % |
| 14/15 | EVAL, 2 | EVEROLIMUS, 1 | 300 | PEG-Acrylate | 3 |
| 16 | EVAL, 2 | EVEROLIMUS, 1 | 300 | N-vinylpyrrolidone | 20 |
| | | | | PEG-Acrylate | 3 |
| 17 | EVAL, 2 | EVEROLIMUS, 1 | 300 | Heparin Benzalkonium Chloride | 3 |
| | | | | PEG-Acrylate | 3 |
| 18 | EVAL, 2 | EVEROLIMUS, 1 | 300 | EVAL | 2 |
| | | | | Heparin Benzalkonium Chloride | 0.7 |
| | | | | PEG-Diacrylate | 0.7 |
| | | | | PEG | 0.7 |
| 19 | EVAL, 2 | EVEROLIMUS, 1 | 300 | EVAL | 7 |
| | | | | Heparin Benzalkonium Chloride | 2 |
| | | | | PEG-Diacrylate | 2 |
| | | | | PEG | 2 |
| 20 | EVAL, 2 | EVEROLIMUS, 1 | 300 | EVAL | 2 |
| | | | | PEG | 0.4 |
| | | | | Heparin Benzalkonium Chloride | 0.2 |
| 21 | EVAL, 2 | EVEROLIMUS, 1 | 300 | EVAL | 3 |
| | | | | PEG | 2 |
| | | | | Sodium Heparin | 2 |
| 22*) | PBT-PEG, 2 | EVEROLIMUS, 1 | 300 | PBT-PEG | 2 |

*)The coating also has a PBT-PEG based primer layer.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A coating for an implantable medical device comprising a first region and a second region above the first region, wherein the first region comprises a therapeutic substance and the second region comprises an interpenetrating polymer network.

2. The coating of claim 1, wherein the medical device is a stent.

3. The coating of claim 1, wherein a diffusion rate of the therapeutic substance in the second region is less than a diffusion rate of the therapeutic substance in the first region.

4. The coating of claim 1, wherein the therapeutic substance is selected from the group consisting of paclitaxel, docetaxel, rapamycin, 40-O-(2-hydroxy)ethyl-rapamycin, 40-O-(3-hydroxy)propyl-rapamycin, 40-O-[2-(2-hydroxy)ethoxy]ethyl-rapamycin, 40-O-tetrazole-rapamycin, and estradiol.

5. The coating of claim 1, wherein the interpenetrating polymer network is formed from a product selected from the group consisting of poly(ethylene glycol)-acrylate, poly(ethylene glycol)-methacrylate, poly(ethylene glycol)-diacrylate, poly(ethylene glycol)-dimethacrylate, N-vinylpyrrolidone, heparin, and heparin derivatives, hyaluronic acid, derivatives of hyaluronic acid, poly(butyleneterephthalate-co ethylene glycol) (PBT-PEG), and mixtures thereof.

6. The coating of claim 5, wherein the derivatives of heparin comprise heparin salts, heparin containing photoactivatable groups, or heparin containing albumin-binding moieties.

7. The coating of claim 6, wherein the heparin salts are selected from the group consisting of sodium heparin, heparin benzalkonium chloride, heparin tridodecyl methyl ammonium chloride, and mixtures thereof.

8. The coating of claim 6, wherein the photoactivatable groups are derived from benzophenone or dithiocarbonate.

9. The coating of claim 1, wherein the second region is an outermost region of the coating.

* * * * *